(12) United States Patent
Whitlock

(10) Patent No.: US 7,820,420 B2
(45) Date of Patent: *Oct. 26, 2010

(54) COMPOSITIONS INCLUDING AMMONIA OXIDIZING BACTERIA TO INCREASE PRODUCTION OF NITRIC OXIDE AND NITRIC OXIDE PRECURSORS AND METHODS OF USING SAME

(76) Inventor: David R. Whitlock, 40 Nash St., Watertown, MA (US) 02472

( * ) Notice: Subject to any disclaimer, the term of this patent is extended or adjusted under 35 U.S.C. 154(b) by 250 days.

This patent is subject to a terminal disclaimer.

(21) Appl. No.: 10/332,933

(22) PCT Filed: Aug. 10, 2001

(86) PCT No.: PCT/US01/25248

§ 371 (c)(1), (2), (4) Date: Jan. 14, 2003

(87) PCT Pub. No.: WO02/13982

PCT Pub. Date: Feb. 21, 2002

(65) Prior Publication Data

US 2004/0014188 A1    Jan. 22, 2004

Related U.S. Application Data

(60) Provisional application No. 60/224,598, filed on Aug. 11, 2000.

(51) Int. Cl.
*C12P 1/04* (2006.01)

(52) U.S. Cl. .......................... 435/170; 435/4

(58) Field of Classification Search .............. 435/6, 435/4, 170; 438/149
See application file for complete search history.

(56) References Cited

U.S. PATENT DOCUMENTS

| | | |
|---|---|---|
| 3,984,575 A | 10/1976 | Farr |
| 4,147,807 A | 4/1979 | Gryczka et al. |
| 4,335,107 A | 6/1982 | Snoeyenbos et al. |
| 4,689,226 A | 8/1987 | Nurmi et al. |
| 4,720,344 A | 1/1988 | Ganczarczyk et al. |
| 5,139,792 A | 8/1992 | Ware et al. |
| 5,176,911 A | 1/1993 | Tosi et al. |
| 5,278,192 A | 1/1994 | Fung et al. |
| 5,314,542 A | 5/1994 | Cassidy et al. |
| 5,322,686 A | 6/1994 | Grahn et al. |
| 5,380,758 A | 1/1995 | Stamler et al. |
| 5,385,940 A | 1/1995 | Moskowitz |
| 5,396,882 A | 3/1995 | Zapol |
| 5,427,797 A | 6/1995 | Frostell et al. |
| 5,451,400 A | 9/1995 | Stern et al. |
| 5,519,020 A | 5/1996 | Smith et al. |
| 5,534,253 A | 7/1996 | Casas et al. |
| 5,570,683 A | 11/1996 | Zapol |
| 5,574,068 A | 11/1996 | Stamler et al. |
| 5,595,753 A | 1/1997 | Hechtman |
| 5,604,127 A | 2/1997 | Nisbet et al. |
| 5,632,981 A | 5/1997 | Saavedra et al. |
| 5,645,839 A | 7/1997 | Chobanian et al. |
| 5,646,181 A | 7/1997 | Fung et al. |
| 5,648,101 A | 7/1997 | Tawashi |
| 5,648,393 A | 7/1997 | Stamler et al. |
| 5,650,447 A | 7/1997 | Keefer et al. |
| 5,665,077 A | 9/1997 | Rosen et al. |
| 5,693,676 A | 12/1997 | Gorfine |
| 5,713,349 A | 2/1998 | Keaney |
| 5,714,511 A | 2/1998 | Saavedra et al. |
| 5,721,278 A | 2/1998 | Garfield et al. |
| 5,725,492 A | 3/1998 | Igo et al. |
| 5,728,705 A | 3/1998 | Lawson et al. |
| 5,765,548 A | 6/1998 | Perry |
| 5,767,160 A | 6/1998 | Kaesemeyer |
| 5,789,447 A | 8/1998 | Wink, Jr. et al. |
| 5,800,385 A | 9/1998 | Demopulos et al. |
| 5,801,203 A | 9/1998 | Lipton |
| 5,807,546 A | 9/1998 | Stern et al. |
| 5,814,656 A | 9/1998 | Saavedra et al. |
| 5,814,666 A | 9/1998 | Green et al. |
| 5,821,112 A | 10/1998 | Botto et al. |
| 5,824,669 A | 10/1998 | Garvey et al. |
| 5,834,030 A | 11/1998 | Bolton |
| 5,839,433 A | 11/1998 | Higenbottam |

(Continued)

FOREIGN PATENT DOCUMENTS

EP    0 780 419    6/1997

(Continued)

OTHER PUBLICATIONS

Catalogue of Bacteria and Phages. 1989. American Type Culture Collection, p. 152, col. 2.*

(Continued)

*Primary Examiner*—Jon P Weber
*Assistant Examiner*—Kailash C Srivastava
(74) *Attorney, Agent, or Firm*—Lando & Anastasi, LLP

(57) ABSTRACT

A method of enhancing health through the generation in close proximity of a surface of a subject, nitric oxide and nitric oxide precursors using bacteria adapted to oxidize ammonia and urea derived from perspiration is described. Local and systemic effects are described including reduction in vascular disease, enhancement of sexual function, improved skin health, and reduced transmission of sexually transmitted diseases.

47 Claims, No Drawings

U.S. PATENT DOCUMENTS

| | | | |
|---|---|---|---|
| 5,849,180 A * | 12/1998 | Sumino et al. | 210/150 |
| 5,849,192 A | 12/1998 | Jagush et al. | |
| 5,858,017 A | 1/1999 | Demopulos et al. | |
| 5,861,168 A | 1/1999 | Cooke et al. | |
| 5,873,359 A | 2/1999 | Zapol et al. | |
| 5,891,472 A | 4/1999 | Russell | |
| 5,895,658 A | 4/1999 | Fossel | |
| 5,900,433 A | 5/1999 | Igo et al. | |
| 5,904,938 A | 5/1999 | Zapol et al. | |
| 5,910,316 A | 6/1999 | Keefer et al. | |
| 5,910,482 A | 6/1999 | Yallampalli et al. | |
| 5,912,019 A | 6/1999 | Singh | |
| 5,958,427 A | 9/1999 | Salzman et al. | |
| 5,994,444 A | 11/1999 | Trescony et al. | |
| 2005/0036996 A1 | 2/2005 | Roussel et al. | |

FOREIGN PATENT DOCUMENTS

| | | |
|---|---|---|
| JP | 59 135845 | 8/1984 |
| WO | WO 98/27991 | 7/1998 |

OTHER PUBLICATIONS atcc.org/common/catalog/wordSearch/results.cfm, total of 4 pages.*
Brochures for Ultra Bac from ABI, Inc., Cleveland, OH.*
Ida et al. 2004. Identification of Genus Nitrosovibrio, Ammonia—Oxidizing Bacteria by Comparison of N-Terminal Amino Acid Sequences of Phosphoglycerate Kinase. Journal of Bioscience and Bioengineering, vol. 98, No. 5, pp. 380-383.*
Head, I.M. et al., 1993. The Phylogeny of Autotrophic Ammonia-Oxidizing Bacteria as Determined by Analysis of 16s Ribosomal RNA Gene Sequences. Journal of General Microbiology, vol. 139, pp. 1147-1153.*
Air Products 2004. MSDS, Version 1.4, Revision Date Apr. 4, 2004, pp. 1-6.*
MedicineNet. 1998. Definition of Vagina. Page 1 of 1. Last Editorial Review: Mar. 26, 1998. http://www.medicinenet.com/script/main/art.asp?articlekey=5951 Printed Nov. 27, 2009.*
atcc.orglcommonlcatalog/wordSearch/results.cfm, total of 4 pages. Undated.*
Brochures for Ultra Bac from ABI. Inc., Cleveland, OH. Undated.*
Database WPI Section Ch, Week 199032 Derwent Publications Ltd., London, GB; Glass D15, AN 1990-242757 XP002290039 & JP 02 169092 A (Mitsubishi Mining & Cement Co.) Jun. 29, 1990.
Bock et al., "Oxidation of Inorganic Nitrogen Compounds as Energy Source", In: The Prokaryotes. A Handbook on the Biology of Bacteria: Ecophysiology, Isolation, Identification, Applications. Edited by Balows et al. Springer-Verlag. Second Edition. 1992, vol. I. Chapter 17, pp. 414-417.

* cited by examiner

COMPOSITIONS INCLUDING AMMONIA OXIDIZING BACTERIA TO INCREASE PRODUCTION OF NITRIC OXIDE AND NITRIC OXIDE PRECURSORS AND METHODS OF USING SAME

This application is a 371 of PCT/US01/25248 filed Aug. 10, 2001 which claims priority to U.S. Provisional Application Ser. No. 60/224,598 filed Aug. 11, 2000.

FIELD OF INVENTION

The present invention relates to a composition including ammonia oxidizing bacteria to increase production of nitric oxide and nitric oxide precursors on the surface of a subject and methods of using same.

BACKGROUND

Beneficial bacteria have been utilized to suppress the growth of pathogenic bacteria. Bacteria and other microorganisms are ubiquitous in the environment. The discovery of pathogenic bacteria and the germ theory of disease has had a tremendous effect on health and disease states. Bacteria are a normal part of the intestinal contents of all living things. These bacteria are not pathogenic under normal conditions, and in fact improve health by rendering the normal intestinal contents less hospitable for disease causing organisms. This is accomplished in a number of ways: nutrients are consumed, leaving less for pathogens; conditions are produced, such as pH, oxygen tension, which are not hospitable for pathogens; compounds are produced that are toxic to pathogens; pathogens are consumed as food by these microorganisms; less physical space remains available for pathogens; and specific binding sites are occupied leaving fewer for pathogens. The presence of these desirable bacteria is seen as useful in preventing disease states.

Fermentation of food products has been done to substitute a desired non-pathogenic strain for potential spoilage or pathogenic organisms. Brewed beverages, wine, pickled food, fermented milk products including cheese, yogurt, buttermilk, sausage are all examples where desired microorganisms are deliberately inoculated into food products under conditions that favor their growth and inhibit the growth of spoilage and pathogenic strains. U.S. patents disclosing the use of specific bacteria to inhibit the growth of harmful bacteria include: U.S. Pat. No. 3,984,575 issued to Farr Oct. 5, 1976; U.S. Pat. No. 4,689,226 issued to Nurmi, et al. Aug. 25, 1987; U.S. Pat. No. 5,322,686 issued to Grahn, et al. Jun. 21, 1994; U.S. Pat. No. 5,451,400 issued to Stern, et al. Sep. 19, 1995; U.S. Pat. No. 5,604,127 issued to Nisbet, et al. Feb. 18, 1997; and U.S. Pat. No. 5,807,546 issued to Stern, et al. Sep. 15, 1998.

U.S. Pat. No. 5,176,911 issued to Tosi, et al. Jan. 5, 1993 discloses the use of specific bacteria recovered from healthy asymptomatic patients and characterized in the laboratory as a preventative and curative topical application to the vaginal area of women suffering from vaginal yeast infections.

U.S. Pat. No. 5,534,253 issued to Casas, et al. Jul. 9, 1996, discloses administering a specific Lactobacillus reuteri strain through external spraying, incorporation into feed, or injection into eggs, to produce an antibiotic substance identified as .beta.-hydroxypropionaldehyde.

U.S. Pat. No. 6,080,401 issued to Reddy, et al. Jun. 27, 2000, discloses the addition of various probiotics to herbal and pharmaceutical drugs to increase their efficacy. The probiotic is selected from the group consisting of non-pathogenic members of genus *Lactococcus, Lactobacilius, Pediococcus, Streptococcus, Propionibacterium, Brevibacterium, Penicillium*, and *Saccharomyces*, and mixtures thereof. In the examples, the bacteria are ingested along with the drug or used in a tooth cleaning preparation.

SUMMARY

The present invention relates to a method of supplying a nitric oxide compound to a subject by positioning ammonia oxidizing bacteria in close proximity to the surface of the subject.

Another embodiment of the present invention relates to an article of clothing treated with bacteria adapted to metabolize any of ammonia, ammonium salts, or urea into nitric oxide and/or nitric oxide precursors.

The present invention is also directed to a preparation to be applied to a surface of a subject comprising ammonia oxidizing bacteria adapted to metabolize any of ammonia, ammonium salts, or urea into nitric oxide and/or nitric oxide precursors.

DETAILED DESCRIPTION

The present invention relates to a to a composition including ammonia oxidizing bacteria to increase production of nitric oxide and/or nitric oxide precursors in close proximity to a surface of a subject and methods of using same. More specifically, applying a composition of an ammonia oxidizing bacteria to skin during or after bathing to metabolize urea and other components of perspiration into nitrite and ultimately into Nitric Oxide (NO) results in a natural source of NO. One aspect of the present invention causes topical nitric oxide release at or near the surface of the skin where it can diffuse into the skin and have local as well as systemic effects. This naturally produced nitric oxide can then participate in the normal metabolic pathways by which nitric oxide is utilized by the body. Adding urea or ammonium salts to the skin provides additional substrates that these bacteria utilize to form nitrite. As used herein, the phrase near the surface is defined as adjacent to or in close proximity to, but need not be in contact with the surface.

The invention is understood by realizing that until the advent of running hot water and soap, bathing was infrequent. Under such conditions (prevailing for >99.9% of historic and prehistoric time) the skin would develop a natural community of microorganisms adapted to the skin environment. An abundant component of human perspiration is urea. In soil, natural bacteria act upon urea and hydrolyze it to ammonia, which is then oxidized to nitrite, followed by rapid oxidation, by still other bacteria, to nitrate. In soil, all nitrogen containing compounds are ultimately degraded to nitrate. In fact it is nitrate that most plants absorb as their nitrogen source. Under conditions of infrequent bathing, skin bacteria that can metabolize urea into nitrite would thrive and proliferate. The resulting nitrite on the skin when dampened by additional perspiration at the normal sweat pH of 4.5 would release NO.

Nitric Oxide is a small molecule that diffuses rapidly through the skin into the capillaries of the skin. Vasodilatation of these capillaries would occur, as well as diffusion of NO into the blood where it may be transported to other regions of the body. Dilatation of the capillaries at the skin surface enhances blood flow to, and hence heat loss from, the skin during periods of exercise.

Heart disease and other vascular diseases are a significant cause of death in the developed world. Vascular diseases also cause significant reductions in quality of life for those afflicted. Significant medical resources are devoted to prevention, treatment and research into the causes of these forms of disease.

Exercise has long been touted as having protective effects on the heart, the vascular system, and on health in general. Numerous studies and reports have shown an inverse correlation between exercise and death from heart disease. Curiously the protective effects of exercise on the vascular system are sometimes seen to be lower at more vigorous activity levels. This diminished protective effect of more vigorous physical activity is not observed in all studies but has been observed for both heart disease and stroke. A recent study, "Physical Activity and Stroke Incidence The Harvard Alumni Health Study", by I-Min Lee, et al. (Stroke. 1998; 29:2049-2054) showed a U shaped curve of stroke incidence verses intensity of exercise. Walking was also observed to reduce stroke incidence independent of other forms of exercise. The authors were unable to explain these observations, nor has a satisfactory explanation of these observations yet been made.

Death rates due to heart disease often show significant seasonal variation. A recent article "Seasonal Variation in Chronic Heart Failure Hospitalizations and Mortality in France", Fabrice Boulay, Md., et al. (Circulation. 1999; 100: 280-286.) shows pronounced increases in mortality during the winter months and declines during the summer months over a 6 year period. This study which covered the entire French population, showed a peak monthly average for January that was 20% above the yearly average. The monthly minimum was 15% below the average in August. This pattern is visible each and every year included in the study but no satisfactory explanation for this data is provided.

Diet, smoking, exercise, control of high blood pressure, being married, personality type, genetic factors, viral infections, moderate alcohol consumption have all been shown to affect rates of heart and vascular diseases. With so many factors being important it is very difficult to find the proper controls to correct for known as well as potential unknown confounding factors. I have found that another factor, which is easily controlled, may explain some of the discrepancy between different rates of vascular disorders.

Physical activity induces a number of physiological changes. As physical exertion increases, heart and respiration rate increase to supply fuel and oxygen to the cells producing work. Since this production of work is not 100% efficient, metabolic heat also increases and must be dissipated. The body increases sweat production to dissipate this heat through evaporative cooling.

While Western medicine has focused on the prompt physiological effects of exercise, sweating per se also has proponents. Raising the ambient temperature, as in a sauna, has been claimed to have salutary effects on one's health. In fact the use of high temperatures to induce sweating has been a common component of personal hygiene in many cultures prior to the introduction of soap and running (hot) water. The Turkish hammam, the Finnish sauna, the Native American sweat lodge, the Russian bania, and the Central American temascal are all examples of the use of high temperature for personal cleansing and hygiene. The Greeks and Roman baths are similar with written records dating from the fifth century BCE. The popular explanation for the health effects of sauna-like treatments has been the "flushing" of toxins out of the body through increased sweating.

While modern medicine has had many advances in the understanding of human physiology, there is still a great deal that remains unexplained. Traditional medicines and practices are often a useful source of compounds and procedures to test for medicinal properties. Thus a method that improves the body's natural ability to regulate and enhance the formation, and release of nitric oxide may have significant and widespread health benefits.

Advances in understanding the interaction of nitric oxide with the physiology of the human vascular system have been made. One advance was the discovery by Drs. Robert F. Furchgott, Louis J. Ignarro, and Ferid Murad that Nitric Oxide is a vasodilator has paved the way for understanding the mechanism of action of organic nitrates, like nitroglycerine, as vasodilators, and for new drugs that increase the time of action of endogenous NO, like Viagra.

Nitric oxide has also been implicated as a component of the human body's natural defense against disease causing organisms. In a book, "Nitric Oxide and Infection", Ferric C. Fang ed., Kluwer Academic/Plenum Publishers, 1999, describes that numerous disease causing organisms cause an increase in nitric oxide production of the body. Evidence suggests that this production is therapeutic, although too much nitric oxide is also implicated in some disease states.

Circadian variation in nitric oxide has been inversely associated with circadian variation in blood pressure. Healthy individuals exhibit higher levels of NO as well as higher circadian variation than individuals with essential hypertension or peripheral arterial occlusive disease. See "Role of Endogenous Nitric Oxide in Circadian Blood Pressure Regulation in Healthy Humans and in Patients with Hypertension Atherosclerosis" Bode-Boger S M, et al. (J Investig Med March 2000; 48(2)125-32). The effects of nitric oxide on the vascular system are described in "Nitric Oxide and the Regulation of the Peripheral Circulation", Phillip J. Kadowitz and Dennis B. McNamara, editors, Birkhauser Boston, 2000, as well as in "The Haemodynamic Effects of Nitric Oxide", edited by Robert T. Mathie and Tudor M. Griffith, Imperial College Press, 1999.

Control and regulation of the generation and release of nitric oxide may provide a method to maintain proper blood pressure, vascular tone, coagulation properties of the blood and a host of other bodily functions. However, nitric oxide has a short lifetime in physiological fluids.

Hemoglobin can reversibly bind nitric oxide to form S-nitrosohemoglobin. This compound forms in one part of the body and is transported by the blood to regions of reduced oxygen partial pressure where it decomposes releasing nitric oxide. The nitric oxide then causes dilatation of the capillaries where the oxygen content of the blood is low. This dilatation increases blood flow to those areas where it is needed most, those areas with reduced oxygen. A known source of S-nitrosohemoglobin is the lungs. Nitric oxide is produced in the nasal passages and is absorbed in the lungs improving the function of the lung by improving the match of blood and air flow. The nitric oxide also has effects on peripheral circulation.

It is known that nitric oxide gas may be administered, and is also generated in nasal passages during inhalation, which is drawn into the lung along with inhaled air. Thus nitric oxide is absorbed in the lung where it attaches to hemoglobin and forms S-nitrosolated hemoglobin. This is a major source of S-nitrosolated hemoglobin producing systemic effects in the body. The following United States patents disclose various physiological effects of nitric oxide inhalation: U.S. Pat. No. 5,427,797 issued to Frostell, et al. Jun. 27, 1995; U.S. Pat. No. 5,765,548 issued to Perry Jun. 16, 1998; and U.S. Pat. No. 5,904,938 issued to Zapol, et al. May 18, 1999.

Topical application of nitric oxide is known. U.S. Pat. No. 5,519,020 issued to Smith, et al. May 21, 1996, discloses the use of nitric oxide releasing materials, placed in close proximity to wounds to enhance healing through a variety of mechanisms. A polymeric material is used to control the rate at which nitric oxide is released because nitric oxide may be toxic and injurious in excessive doses.

U.S. Pat. No. 5,646,181 issued to Fung, et al. Jul. 8, 1997 discloses topical medications containing organic nitric oxide releasing compounds that when topically applied release nitric oxide in sufficient quantities to treat impotence without producing systemic side effects such as hypotension.

U.S. Pat. No. 5,648,101 issued to Tawashi Jul. 15, 1997 discloses products that liberate nitric oxide through reaction of an inorganic nitrite and a ferrous metal salt. These products may be ingested, applied topically, taken as suppositories, applied as transdermal patches, and used in osmotic pumps.

U.S. Pat. No. 5,891,472 issued to Russell Apr. 6, 1999 discloses the use of topically applied nitric oxide donors for the treatment of equine laminitis.

U.S. Pat. No. 5,895,658 issued to Fossel Apr. 20, 1999, discloses the use of topically applied L-arginine, a substrate for production of nitric oxide form nitric oxide synthase to cause local vasodilatation of the skin for the purpose of producing beneficial effects such as warming of cold or cool tissues, growth of hair on the scalp, healing of leg ulcers secondary to diabetes or confinement to bed, as well as beneficial effects through restoration of natural mechanisms based on improvement of local blood supply.

U.S. Pat. No. 5,958,427 issued to Salzman, et al. Sep. 28, 1999, discloses compounds containing nitric oxide donors that do not pass through mucosal membranes but release nitric oxide which does cross through skin or mucosal membranes and provide local effects. These compounds may also be applied topically to the genitalia for used as an aphrodisiac or applied in the mouth for use as antibacterial agents.

U.S. Pat. No. 6,056,966 issued to Selim, et al. May 2, 2000 discloses the use of topical organic nitrates which are nitric oxide donors in the treatment of male impotence. These produce the desired effects without undesired systemic effects including hypotension.

Compounds that release nitric oxide may also be injected into the body of a subject. U.S. Pat. No. 5,721,278 issued to Garfield, et al. Feb. 24, 1998, discloses the use of inhibitors of nitric oxide synthesis to inhibit ovulation, and the use of nitric oxide precursors to bring about ovulation.

U.S. Pat. No. 5,800,385 issued to Demopulos, et al. Sep. 1, 1998, discloses solutions including nitric oxide donors for irrigating the sites of operative wounds. The nitric oxide donors may be included in the solutions for their anti-spasm activity.

U.S. Pat. No. 5,858,017 issued to Demopulos, et al. Jan. 12, 1999, discloses the use of solutions containing among other things, nitric oxide donors in urological irrigation solutions.

U.S. Pat. No. 5,861,168 issued to Cooke, et al. Jan. 19, 1999 discloses the intramural application of nitric oxide precursors during coronary balloon angioplasty to reduce thickening of the treated vessels and to improve tolerance to the angioplasty procedure.

It is known to use nitric oxide to treat a variety of conditions. U.S. Pat. No. 5,278,192 issued to Fung, et al. Jan. 11, 1994, discloses using organic nitrates for continuous treatment of conditions including, angina, particularly chronic, stable angina pectoris, ischemic diseases, congestive heart failure, for controlling hypertension and/or impotence in male patients. These organic nitrates may be administered in a variety of ways including sublingual, oral and buccal tablets as well as capsules, topical creams and ointments, patches, tapes, spray and intravenous solutions.

U.S. Pat. No. 5,385,940 issued to Moskowitz Jan. 31, 1995 discloses the administering nitric oxide donors or L-arginine to act as the substrate of nitric oxide synthase during a stroke to increase nitric oxide production and so cause vasodilatation to reduce the infarct size.

U.S. Pat. No. 5,632,981 issued to Saavedra, et al. May 27, 1997, discloses polymers containing bound nitric oxide releasing compounds.

U.S. Pat. No. 5,645,839 issued to Chobanian, et al. Jul. 8, 1997 disclose the use of nitric oxide donors and precursors combined with angiotensin converting enzyme inhibitors to suppress and reverse fibrosis in the body, wherein the fibrosis is associated with a disorder selected from the group consisting of cardiovascular fibrosis, arterioscleriotic disorders, pulmonary fibrosis, adult respiratory distress syndrome, inflammatory disorders, scleroderma, cirrhosis, keloids, and hypertrophic scars.

U.S. Pat. No. 5,648,393 Stamler, et al. Jul. 15, 1997 disclose the use of S-nitrosylated compounds to treat impotence.

U.S. Pat. No. 5,650,447 Keefer, et al. Jul. 22, 1997 discloses the use of polymers containing bound nitric oxide releasing compounds to treat restenosis when incorporated into devices such as sutures, vascular implants, stents, heart valves, drug pumps, drug-delivery catheters, self-adhering means such as endoluminal implants, liposomes, microparticles, microspheres, beads, disks or other devices.

U.S. Pat. No. 5,789,447 issued to Wink, Jr., et al. Aug. 4, 1998, discloses a method of reducing free radical induced tissue damage associated with ischemia reperfusion injury wherein the ischemia reperfusion injury is associated with a condition or disease selected from the group consisting of transplantation, trauma, inflammation, stroke, seizure, rheumatoid arthritis, atherosclerosis, cancer, dementia, diabetes, hypertensive crisis, ulcers, lupus, sickle cell anemia, ischemic bowel syndrome, pulmonary emboli, Ball's syndrome, pancreatitis, heart attack, and aging.

U.S. Pat. No. 5,814,666 issued to Green, et al. Sep. 29, 1998, disclose the use of nitric oxide releasing compounds as antimicrobial agents.

U.S. Pat. No. 5,910,316 issued to Keefer, et al. Jun. 8, 1999 discloses the use of a nitric oxide releasing agent directly applied to the penis by delivery means being selected from the group consisting of a transurethral applicator, a penile implant, a dermal patch and a condom.

U.S. Pat. No. 6,057,367 issued to Stamler, et al. May 2, 2000 disclose using a variety of methods to manipulate nitrosative stress. These methods include using acidified nitrite as a mouth rinse and a mixture of acidified nitrite plus a thiol as a topical application. S-nitrosothiol may be applied topically or formed in situ from an inorganic nitrite, a pharmacologially acceptable acid and a thio. Pathenogenic microbes may also convert substrates to nitrosating agents which inhibit the growth of the pathenogenic microbe.

In the book, "Nitric Oxide and Infection", Ferric C. Fang ed., Kluwer Academic/Plenum Publishers, 1999, in a chapter titled "Nitric Oxide and Epithelial Host Defense" by Nigel Benjamin and Roelf Dykhuizen, the authors discusses their findings of nitric oxide production on the skin, the importance of this in normal infection control, and their finding that a salve containing acidified nitrite is effective in the treatment of tinea pedis (athlete's foot). They attribute the normal production of nitrite on the skin to the reduction of sweat nitrate to nitrite by skin bacteria. Many heterotrophic bacteria will reduce nitrate to nitrite, for example, E. coli. These bacteria are facultative anaerobes that normally utilize oxygen as the electron sink for their cellular respiration, but can also utilize nitrate in the absence of oxygen. All these bacteria utilize organic substrates for energy and growth and many of these bacteria can be pathogenic. In the mouth, salivary nitrate is reduced by these facultative anaerobes. These nitrate reducing bacteria are kept anaerobic by the layers of biofilm that accumulates on the tongue. In that the surface of the skin is expected to be aerobic, reduction of nitrate to nitrite should be minor. While some nitric oxide may be produced by bacterial reduction of sweat, the urea content of sweat is much higher than that of nitrate. I have found a more significant source that is more easily and safely stimulated is the utilization of urea in sweat to form nitrite through ammonia and urea oxidizing bacteria.

Nitrate in the diet is rapidly absorbed and is concentrated by the body in the saliva. In the mouth facultatively anaerobic bacteria on the tongue metabolize nitrate to form nitrite. Saliva contains significant nitrite and studies have shown that when the skin is licked that NO is released. This NO is believed to have anti-microbial and vasodilator effects. The release of NO is the rationalization as to why animals (and humans) lick wounds to enhance healing. Similarly a common folk remedy for impotence is the use of saliva directly applied to the penis where NO release would induce and prolong erection.

In their chapter, Benjamin and Dykhuizen, in discussing the role that salivary nitrite has in reducing food born illness, point out that in the stomach, chloride is present in a high concentration and will catalyze nitrosation reactions to form additional reactive intermediates that may add to the toxicity of acidified nitrite. On the skin, the concentration of chloride can reach that of a saturated salt solution, levels much higher than can be reached in the stomach.

Bathing has as one of its primary objectives removing bacteria from the skin. While pathogenic bacteria are undesirable, all bacteria are not pathogenic. Recent advances in soap formulations have included the adding of broad-spectrum anti-microbial agents to soap. Bathing has greatly reduced the incidence of water-borne diseases such as cholera and various diarrhea diseases. It may be that removal of all bacteria has the undesired effect of removing the natural bacteria that produce nitrite, which the body has evolved to utilize physiologically.

With this in mind a number of curious aspects of human physiology can be understood. The areas of the body that are most in need of rapid healing, infection control and hence of NO production are feet, hands, scalp, and genital area, which are the parts of the body where perspiration is most abundant even when not needed for cooling. This may be why there is urea, chloride, and iron in perspiration, and why perspiration has a low pH.

Sauna and other types of sweat baths can be seen as ways of enhancing the production of nitrite and NO on the skin. Modern use of the sauna as part of a bathing ritual involving washing with soap and running water would not achieve such a result and has only been practiced since the 19$^{th}$ century. Urea and nitrite are very water soluble and would be washed off readily. When the custom of sauna first developed over 2000 years ago, there was no running hot water, so the skin would retain the soluble urea and nitrite, and without soap the bacteria would also be retained.

Another custom, the use of a whisk, a bundle of birch branches used to gently beat the skin, can be seen as a method of inoculating the skin with bacteria present on the whisk. Between uses the whisk would dry out and the bacteria surviving would necessarily become adapted to living on perspiration residues under fairly dry conditions, the natural state of human skin. The advent of the germ theory and the perceived need for aseptic hygienic conditions has modified the use of such devices to where they probably no longer serve this original function.

The beneficial health effects of sweating can be seen as deriving from the increased production and release of NO on the skin, rather than due to removal of wastes. Perspiration as a waste removal method would seem to be a non-intuitive and ineffective method. Most sweating occurs during periods of high metabolic load, which would seem to be an inopportune time to use any metabolic capacity to rid the body of waste products. In fact the kidneys shut down under conditions of insufficient heart output. Sweat output can vary greatly from day to day, hour to hour, and minute to minute. Accumulating wastes in anticipation of episodic sweating events would seem to be a poor allocation of resources. Nervous sweating that occurs in anticipation of stressful events may be the body's way or preparing itself for a stressful event. Dampening the skin with perspiration would release NO from the newly generated and accumulated nitrite that would then act as a vasodilator, which may enhance blood flow and prepare the body to respond effectively to the stressor. Organic nitrates like nitroglycerine are often prescribed for exactly such use prior to physical or emotional stress to achieve just such vasodilatation.

Sweating can then be seen as the solution to skin disorders, rather than as the cause. If the ammonia and urea oxidizing bacteria content of the skin were restored to pre-industrial levels, then areas of the body with profuse sweating would also have profuse nitrite and NO production and would be expected to heal faster, better resist infection, and be in a better general state of health. In the absence of such bacteria, which happen to be relatively slow growing, other faster growing heterotrophic bacteria would hydrolyze urea to free ammonia which is quite toxic and irritating to the skin. It is thus the absence of the proper bacteria that cause perspiration residues to become irritating. Oxidation of ammonia to nitrite or nitrate lowers the pH, and converts any remaining free ammonia to the less toxic ammonium ion.

After formation on the skin, nitric oxide may diffuse into the capillaries of the skin and be taken up by the blood. The capillaries of the skin may dilate in response, and some of the nitric oxide may be taken up by hemoglobin to form S-nitrosohemoglobin which will circulate though out the body and have systemic effects.

A region of the skin that is thin and has abundant blood capillaries is the skin of the head and scalp. The presence of hair on the head is often rationalized as limiting heat loss. But one wonders why the scalp has hair to prevent heat loss while the rest of the body remains essentially hairless. There is significant heat loss from the head, possibly a result of the skin of the scalp being thin so as to allow the rapid diffusion of nitric oxide into the blood. The blood from the scalp joins that from the brain before entering the heart and lungs. The blood supply of the brain is among the most critical to the body and shows little variation even during periods of extreme metabolic stress. Combining blood having low oxygen tension from the brain with blood having a high nitric oxide content from the scalp may be an efficient use of the nitric oxide so produced. Because nitric oxide may also be released into the air around the head and face, where air drawn in during breathing in close proximity to a source of nitric oxide, the concentration of nitric oxide would increase in inspired air. The different patterns of facial hair seen between men and women may derive from different patterns of peak metabolic activity, men during hunting and fighting and women during pregnancy, labor and childbirth. Just as inhaled nitric oxide is protective of pulmonary hemorrhage for horses, nitric oxide released by bacteria on facial hair may facilitate greater levels of physical exertion.

Many of the veins of the scalp drain through the skull into the vascular sinuses in the brain. The arteries bringing blood to the brain pass through these same sinuses. This contact may be so that nitric oxide may diffuse from the venous blood leaving the scalp into the arterial blood entering the brain. Such diffusion would help explain the protective effect of moderate exercise on stroke. Sweat on a head would then reduce the vascular resistance in the brain.

Hair can be seen as an insulating material but also as a surface on which ammonia oxidizing bacteria may proliferate. Hair may also be an absorbent material to prevent sweat from dripping off and may also provide a suitable microclimate for the ammonia oxidizing bacteria. Nervous sweat is mediated through the adrenergic pathway and typically stimulates sweat on the head and neck.

Sweating for non-cooling purposes can be seen as a natural way for the body to increase nitric oxide production. The malaria causing organism is affected by nitric oxide, and when nitric oxide synthase inhibitors are given to animals with malaria, the mortality is increased. The excessive sweating that is one of the symptoms of malaria (and of many other infections) can be seen as one of the body's natural nitric oxide increasing mechanism.

Human sweat has a high concentration of lactic acid. This renders the normal pH of sweat in the 4.5 range, where nitrite rapidly decomposes to release NO. Sweat also contains abundant iron. A quarter of ingested iron is excreted in the sweat. Iron is well known to coordinate with NO and form ironnitrosyl complexes. Nitric oxide also reacts with superoxide to form peroxynitrite. In aqueous solution iron catalyzes reactions of peroxynitrite with other compounds to form toxic products. The presence of abundant iron and nitrite on the skin may be the first line of defense against skin infections.

Because the outer layers of skin are non-living, pickling and curing of these dead layers with nitric oxide prior to their sloughing off should have no detrimental health effects. Indeed, depending on bacteria for nitrite production and hence NO production, no living part of the body need be exposed to high levels of nitrite or nitric oxide or toxic NO reaction products. Levels can be reached on the skin what would be detrimental to living tissues. This may be a very effective way of warding off skin infections, and may be the system that humans have evolved to utilize in the absence of frequent bathing.

The effect of exercise on vascular disease can also be seen in a new light. Moderate activity is both exercise and a way of, through inducing perspiration, increasing NO production. Vigorous activity does these things also, but if the sweating is sufficiently profuse, bathing is generally done after the exercise. Washing away the perspiration removes the protective effect of this NO production. This explains the reduced protective effect of vigorous exercise when compared with moderate exercise seen in some studies. The protective effect of exercise is increased but the protective effect of NO is reduced by bathing. That may indicate that the beneficial health effect of skin bacteria derived NO is, at least in some people, of comparable magnitude to that of exercise.

Reduced incidence of heart disease in summer may be due to the increased amount and time that sweat stays on the skin. In that the ammonia oxidizing bacteria are slow growing, they can easily be washed off faster than they can proliferate. That an annual pattern can be seen in the incidence of heart disease is strong evidence that this effect is substantial.

Nitrite can be generated in several ways by bacteria. The first is by the oxidation of ammonia or urea. This is the necessary first step in the nitrification of ammonia in soil. Specific autotrophic bacteria utilize this ammonia oxidation to provide all their metabolic energy needs. A second type of autotrophic bacteria utilize this nitrite and further oxidize it to nitrate and utilize this energy for their metabolism. Other bacteria including heterotrophic bacteria can utilize nitrate to oxidize other compounds while reducing the nitrate to nitrite. At or below pH 5.5 nitrite decomposes releasing NO.

The reduced incidence of heart disease may be due to nitric oxide derived from the bacterial reduction of nitrate or to the bacterial generation of nitrite from ammonia or urea. Autotrophic bacteria are only expected to proliferate if there is a long interval between bathing, weeks or more, so that much of the observed differences in incidence is likely due to nitric oxide derived from sweat nitrate. However, the use of ammonia oxidizing bacteria in the present invention would allow for higher levels and larger effects on vascular health.

Similar processes are used to generate nitric oxide that is used in curing meat. General properties of nitric oxide, physiological properties, chemical properties, and its role and mechanism of action in food preservation is well described in a book "Nitric Oxide Principals and Actions", edited by Jack Landcaster, Jr., Academic Press, 1996. Heterotrophic bacteria, to achieve a low pH and to produce nitrite from nitrate, are commonly used in meat preserving where nitrate in a pickling brine is reduced to nitrite, releasing NO which reacts with meat to produce the characteristic color and flavor of cured meat. In meat preserving, these bacteria are added as a pure culture where they retard the undesirable growth of disease and spoilage bacteria. Micrococcus varians is sometimes used for this purpose as described in U.S. Pat. No. 4,147,807 issued to Gryczka, et al. Such bacteria, as a normal component of food, would not be expected to cause any adverse health effects when applied to the skin or when accidentally ingested. Applying such bacteria to the skin would enhance the production of nitric oxide on the skin through the reduction of nitrate to nitrite. Some heterotrophic bacteria can produce nitrite from ammonia, but their oxidation of ammonia is substantially slower than that of the autotrophic lithotrophic ammonia oxidizers.

In the environment, ammonia and urea are oxidized to nitrite by *Nitrosomonas, Nitrosococcus, Nitrosospira, Nitrosocvstis, Nitrosolobus,* and *Nitrosovibrio*. These bacteria are all lithotrophic Gram-negative bacteria that utilize carbon dioxide as their major carbon source. In the environment nitrite is oxidized to nitrate by *Nitrobacter* and *Nitrocystis*. *Nitrosomonas* is the most abundant of these types in soil and would be expected to be the most abundant on normal skin. These bacteria are autotrophs, that is, they do not utilize organic carbon for energy although some can assimilate organic carbon to a limited extent which can stimulate growth. All metabolic energy is obtained from the oxidation of the nitrogen containing species. The majority of carbon derives from the fixing of carbon dioxide utilizing this energy. Because these bacteria need only ammonia, oxygen, inorganic minerals, and carbon dioxide, they are expected to be completely non-pathogenic. The only part of the body where all of these are available is the exterior of the skin. They are slow growing when compared to other bacteria. Where *E. coli* has an optimum doubling time of 20 minutes, *Nitrosomonas* has an optimum doubling time of 10 hours. Because they do not utilize glucose or other organic compounds, they are difficult to culture and do not grow on the standard media used for isolating pathogens, which do utilize organic substrates for energy and growth. Some strains can also utilize urea directly.

These autotrophic ammonia oxidizing bacteria can be stimulated by applying to the skin nutrients needed by these bacteria such as those nutrients found in American Type Culture Collection standard culture media, including ATCC 1953, ATCC 928, ATCC 1573, ATCC 221, ATCC 929, including, for example, urea, ammonium salts, sodium, potassium, magnesium, calcium, phosphate, chloride, sulfate, trace mineral salts including iron, copper, zinc, cobalt, manganese, molybdenum and buffers. Application of a preparation or solution comprising some or all of those nutrients to the skin and scalp would stimulate the naturally occurring autotrophic bacteria, forming nitrite and nitric oxide without stimulating heterotrophic bacteria.

*Nitrobacter* are inhibited by elevated pH and by free ammonia. In soil this can lead to the accumulation of nitrite in soil which is quite toxic when compared to nitrate. On the skin, addition of an alkaline agent would raise the pH and inhibit the oxidation of nitrite allowing higher concentrations to develop. Thus using an alkaline compound could serve to increase the concentration of nitrite. Talc while being essentially neutral often contains calcium and magnesium carbonates as impurities. Small amounts of these may then make the skin alkaline when dry, but upon sweating the pH would drop and the increased nitrite would be available for conversion to NO. Inhibiting bacteria such as *Nitrobacter* that reduce the nitrite concentration on the skin is a useful method to further enhance nitric oxide release. Alternatively, *Nitrobacter* may be included, which will then increase the production of nitrate. Then other bacteria utilizing this nitrate and the other organic compounds on human skin to form nitrite can be used.

Bacteria that are useful in this regard are bacteria that metabolize the normal constituents of human perspiration into NO precursors. These include, for example, urea to nitrite, urea to nitrate, nitrate to nitrite, urea to ammonia, nitrite to nitrate, and ammonia to nitrite. In some cases a mixed culture is preferred. The bacteria can conveniently be applied during or after bathing and can be incorporated into various soaps, topical powders, creams, aerosols, gels and salves. One aspect of the invention contemplates application to body parts that perspire the most, such as, for example, hands, feet, genital area, underarm area, neck and scalp. The major difference between these different areas of the skin is the activity of water. The skin of the hands is much drier than that of the feet, normally covered with socks and shoes, due to the increased exposure of the hands to the drying effects of ambient air. It is contemplated that different strains of bacteria may work best on different areas of the body, and a mixed culture of all the types would allow those that grow best to proliferate and acclimate and become the dominant culture present in a specific area. Clothing may also be worn to change the local microclimate to facilitate the growth of the desired bacteria. For example, wearing a hat may simulate dense hair and help to maintain the scalp in a warmer and moister environment.

Because a normal skin environment is relatively dry, bacteria adapted to low water tension environments are advantageous. One example of a moderately halophilic ammonia oxidizing bacteria is *Nitrosococcus mobillis* described by Hans-Peter Koops, et al. (Arch. Microbiol. 107, 277-282 (1976)). This bacteria has a broad range of growth. For example, while the optimum pH for growth is 7.5, at pH 6.5 it still grows at 33% of its maximal rate. Another more halophilic species, *Nitrosococcus halophillus* described by H. P. Koops, et al. (arch. Micorbiol. (1990) 154:244-248) was isolated from saturated salt solutions in a natural salt lake. *Nitrosococcus oceanus* (ATCC 1907) is halophilic but has an optimum salt concentration intermediate between the other two. The optimum NaCl concentrations for the three are 200, 700, and 500 mM NaCl respectively. *N. oceanus* however utilizes urea and tolerates ammonia concentrations as high as 1100 mM as ammonium chloride. While growth at optimum conditions is the fastest, similar results may be achieved by using more bacteria. Thus while the optimum pH for growth of *N. mobillis* is 7.5, one can achieve the same nitrite production by using 3 times as many bacteria at pH 6.5. Because the quantities of bacteria in the present invention may be large, a number of orders of magnitude larger than that which occurs within 24 hours of bathing, the fact that the pH of the skin is not optimum for these bacteria is not an inhibition to their use. Because *N. halophillus* was isolated from a saturated salt solution, it should easily survive the relatively moister human skin environment.

Some bacteria produce nitric oxide directly. One example is described in "Production of nitric oxide in *Nitrosomonas europaea* by reduction of nitrite", by Armin Remde, et al. (Arch. Microbiol. (1990) 154:187-191). *N. europaea* as well as *Nitrosovibrio* were demonstrated to produce nitric oxide directly. *Nitrosovibrio* is often found growing on rock where the acid generated causes corrosion. It has been suggested by Poth and Focht, "Dinitrogen production from nitrite by a *Nitrosomonas* isolate." (Appl Environ Microbiol 52:957-959), that this reduction of nitrite to volatile nitric oxide is used as a method for the organism to eliminate the toxic nitrite from the environment where the organism is growing, such as the surface of a rock.

Any ammonia oxidizing bacteria may be used in the present invention. In a preferred embodiment, the ammonia oxidizing bacteria may have the following characteristics as are readily known in the art: ability to rapidly metabolize ammonia and urea to nitrite and other NO precursors; non pathogenic; non allergenic; non producer of odoriferous compounds; non producer of malodorous compounds; ability to survive and grow in human sweat; ability to survive and grow under conditions of high salt concentration; and ability to survive and grow under conditions of low water activity.

Natural bacteria can be used as well as bacteria whose characteristics have been altered through genetic engineering techniques. Bacteria culturing techniques can be used to isolate strains with the above characteristics. A mixture of pure strains would avoid the problems associated with simply culturing bacteria from the skin, which includes the potential growth of pathogens and other bacteria having undesirable characteristics. However, culturing bacteria from the skin and growing them on growth media that simulates the composition of human perspiration may also be effective at increasing the nitric oxide production rate. A useful method for culturing and isolating such bacteria is to grow them on media containing urea and ammonia plus mineral salts, but without the organic compounds that heterotrophic bacteria utilize, such as sugars and proteins. When isolating autotrophic ammonia and ammonia oxidizing bacteria, it may also be desirable to attempt growth on a heterotrophic media to verify that the autotrophic strain is not contaminated with heterotrophic bacteria.

U.S. Pat. No. 4,720,344 issued to Ganczarczyk, et al. Jan. 19, 1988, discloses the operation of a waste water treatment facility under conditions that maximize the conversion of ammonia to nitrite while minimizing the conversion of the resulting nitrite to nitrate. This is accomplished by utilizing conditions that are conducive to the growth of *Nitrosomonas* but not to *Nitrobacter*. This is accomplished most preferably by adjusting the pH and ammonia content of the waste water to levels that are conducive to the growth of *Nitrosomonas* but not to *Nitrobacter* and then adjusting the hydraulic retention times in the contacting chambers to less than the recovery time of the inhibited bacteria.

U.S. Pat. No. 5,314,542 issued to Cassidy, et al. May 24, 1994, discloses the growth and treatment of bacterial cultures of *Nitrosomonas* to allow for extended shelf life in a dormant state and subsequent treatment to produce rapid recovery of metabolic activity.

U.S. Pat. No. 5,139,792 issued to Ware, et al. Aug. 18, 1992, discloses a method of dispensing specific bacteria into animal feed and drinking water without agitation to maintain the bacteria in suspension.

An analogous method of treatment of ammonia oxidizing bacteria cultures is also useful in the present invention where ammonia oxidizing bacteria are grown in a media, concentrated and separated from the media, suspended in sterile water with the proper salt concentration, stored under aseptic conditions, reviving the bacteria through addition of ammonia, and then applied to the skin.

Methods of isolation of useful bacteria suitable for colonization of human skin are analogous to methods used for the isolation of bacteria suitable for colonization of livestock digestive systems. Scrapings are collected from healthy individuals, inoculated into suitable media, grown and characterized. Steady state continuous culture methods can be used to ensure stability of the culture over time.

A useful method of treatment of ammonia oxidizing bacteria cultures, along the lines of Cassidy, et al. in U.S. Pat. No. 5,314,542, is where ammonia oxidizing bacteria are grown in a media, concentrated and separated from that media, suspended in sterile water with the proper salt concentration, stored under aseptic conditions, revived through addition of ammonia, and held for a period of time for the bacteria to become active. Cassidy, et al. utilize their bacteria culture and storage method for bacteria used for ammonia control in aquaria. A similar method of growing and treating bacteria can be used to produce bacteria which can then be used in the present invention and applied to the skin.

The ammonia oxidizing bacteria are aerobes which requires oxygen for their metabolism and cannot grow in anaerobic conditions. However many of them can also use nitrate as well as oxygen as the terminal electron sink of their metabolic processes. Storage for prolonged periods of time in a sealed container runs the risk of the container becoming anoxic. Nitrate can be added to the fluid in the container so that nitrate can be utilized instead of oxygen for bacteria respiration during storage allowing for non-fluid formulations such as gels and sticks. Bacteria on the interior of such formulations can derive their oxidizing substrate from dissolved nitrate in the absence of dissolved oxygen.

In another embodiment of the present invention, urea, nitrite and nitrate, iron, lactic acid, and salt may be included in a compound comprising the bacteria or applied separately to supplement the skin, because bathing removes these water soluble compounds. The bacteria may also be applied during or after bathing and may be incorporated into various topical powders, creams, sticks, aerosols, and salves. Other compounds may be added to these cosmetic preparations as selected by one skilled in the art of cosmetic formulation such as, for example, water, mineral oil, coloring agent, perfume, aloe, glycerin, sodium chloride, sodium bicarbonate, pH buffers, UV blocking agents, silicone oil, natural oils, vitamin E, herbal concentrates, lactic acid, citric acid, talc, clay, calcium carbonate, magnesium carbonate, zinc oxide, starch, urea, and erythorbic acid.

The ammonia oxidizing bacteria, may be applied to any surface of a subject, such as, for example, skin and hair. In a preferred embodiment, the bacteria is applied to the skin of a subject. In a more preferred embodiment, the ammonia oxidizing bacteria may be applied to the scalp because the scalp provides excellent blood supply. Bacteria may be incorporated into various hair treatments and devices, including conditioners, gels, hair sprays, hair nets, combs, brushes, hats, hair pieces.

Another embodiment of the invention includes analogous methods used for curing meat, since the goal of meat curing is the production of nitric oxide. These pickling brines and curing compositions are expected to present little health risk since they are considered safe for human consumption. In particular, when nitrite is treated with ascorbic acid, nitric oxide is produced. Nitrite is reduced by ascorbate to generate nitric oxide. Usually in modern meat curing, ascorbate or erythorbate are used with nitrite to generate nitric oxide. In meat preserving, nitric oxide is a precursor in a chain of chemical reactions leading to the development of specific flavors and colors. At low pH, such as less than 5, nitric oxide is rapidly lost from pickling brines before these chemical reactions can occur. Therefore, a higher pH is recommended for meat preserving. Mixtures of nitrite with erythorbate may be one such example. Combining meat curing formulations with cosmetic type formulations may achieve a similar benefit. Combining bacteria, urea, and erythorbic acid may be a preferred combination. Other physiologically acceptable acids may be used as well.

An advantage of an embodiment of the invention is that the induced NO production is under physiological control through sweating. Organic nitrates, such as nitroglycerine, are sometimes prescribed for use prior to time of emotional or physical stress. These are the same conditions under which nervous sweating occurs. One aspect of the present invention may be a reduced incidence of heart disease, vascular diseases, impotence, and infertility. Any condition that may be treated through a NO enhancing method may be amenable to treatment with present invention, even where known treatments include administering nitric oxide or NO donor substances orally, topically, sublingually, nasally, by injection, by inhalation. For example, impotence is treated with Viagra, which extends the duration of action of NO. Use of the present invention may reduce the need for the use of agents such as Viagra.

Individuals need not have clinical symptoms of any of these disorders in order to benefit from the present invention. The invention may be used as a preventative measure along the same lines as proper diet, taking vitamins, exercising, or as bathing in general. Because disorders are related through the common action of the vasodilator NO, one can use the invention for heart disease prevention and receive a therapeutic value for impotence. Because impotence is a disorder that is often stigmatized, an impotence treatment that can be disguised as a general health tonic is advantageous.

In another embodiment of the invention, the bacteria is applied to the surface of non-human vertebrates. Domesticated animals such as horses, dogs, pigs, and chickens are seen to roll in and cover themselves with dirt. In that urea is an abundant compound in urine and manure, bacteria adapted to living in barnyard soil would be expected to be rapid metabolizers of urea into nitrite. Wild animals also cover themselves with dirt. A component of such behavior is likely the inoculation of the skin or fur with bacteria that will metabolize sweat components into NO and NO precursors. Using a substantially pure culture of such bacteria would improve the health of domesticated animals and facilitate their growth. Ammonia is often present in large amounts in animal feed lot areas. Bacteria that would metabolize ammonia into NO or NO precursors would reduce the ill effects of ambient ammonia and improve the economics of intensive animal farming. Other subjects are for example, vertebrates such as, domesticated, laboratory, transgenic, chimeric, and zoo animals such as, horse, pig, cow, dog, cat, goat, sheep, buffalo, donkey, mule, elephant, cat, wolf, camel, llama, chicken, turkey, primates, ungulates, rodents, chimpanzees, gorilla, orangutan, mice, rats, and rabbits.

The practice of some animals, to deposit their urine and feces in a single location can be seen as their instinctive production of a rich environment for the culturing and proliferation of nitrite producing bacteria. That animals instinctively exhibit behaviors that re-inoculate their skins with these bacteria would indicate that these bacteria can be readily lost from the skin and that re-inoculation is necessary for animals. In that humans typically bathe more frequently than animals, the human need for re-inoculation is correspondingly greater.

Treatments for foundering or equine laminitis as described in U.S. Pat. Nos. 6,045,827 and 5,891,472 issued to Russell; Meri Charmyne both titled "Treatment of equine laminitis" include the treatment of this condition with nitric oxide donors applied topically to the affected areas. This serious disease of horses is treated through application of a nitric oxide donor to the feet and hoof region. Nitroglycerine has been used, as have other nitric oxide donors. Horses instinctively accomplish this in the wild by urinating in the mud, allowing nitrite forming bacteria to proliferate, and walking through this mud containing the nitrite producing active cultures. Modern stable practices call for good house keeping and the elimination of any accumulation of urine and feces where horses walk. All hoofed animals are subject to similar disorders of the feet and hooves. Thus all hoofed animals may benefit from application of the suitable ammonia oxidizing bacteria.

U.S. Pat. No. 5,765,548 issued to Perry discusses the use of nitric oxide mixed with air breathed by the horse during vigorous exercise and the use of nitric oxide augmenters injected prior to exercise as beneficial in reducing the incidence and severity of exercised induced pulmonary hemorrhaging. Significant reductions in capillary pressure were demonstrated by Perry. Application of an appropriate ammonia oxidizing bacteria to the horse's skin may have the effect of increasing the natural production of nitric oxide during exercise. This nitric oxide may diffuse through the horse's skin and be absorbed into the blood where it would circulate resulting in systemic effects. Some nitric oxide would also be released into the air around the horse and would be inhaled. Presumably decreased pressure drop translates into increased maximal flow of air and blood in the lungs, and hence increased maximal exercise performance. Achieving this increased performance through natural means would be advantageous in horse racing. Similarly racing gray hounds, draft animals, beasts of burden, and animals under stress may also have their nitric oxide production enhanced. Human athletes may similarly enhance their performance by utilizing skin bacteria to augment nitric oxide production before, during and after exercise. Typical athletic events include, for example foot races, weight lifting, bicycle race or practice, football game or practice, soccer game or practice, basket ball game or practice, baseball game or practice, golf game or practice, mountain climbing, boxing match or practice, hockey game or practice, and tennis match or practice.

The ammonia oxidizing bacteria may be positioned in close proximity to a surface of a subject by being applied directly or indirectly to the surface of the subject. Suitable bacteria may be positioned in close proximity to the surface of the subject by being indirectly applied by application to articles with which the surface of the subject comes into contact, such as, for example, bedding products such as straw, wood shavings, pillows, sheets, habitat enclosures, stalls, brushes, combs, and mattresses. Similarly suitable bacteria can be added to litter box products so that when the animal comes into contact with the litter and litter box, the animal subject will be in close proximity to the bacteria. As an added feature of such litter box products the urea in urine may be oxidized to non-volatile products and the ammonia smell of litter boxes will be reduced. Rather than give off ammonia, the litter boxes would give off nitric oxide which would enhance the pulmonary function of animals and humans in the vicinity, as well as provide systemic effects.

In one aspect of the invention, an article is treated with ammonia oxidizing bacteria. For example the article may be coated or impregnated with the bacteria. In a preferred embodiment, the article treated with the bacteria, contacts a surface of a subject, such as, for example, clothing, collar, and saddle.

Articles contacting the surface of a human subject, such as a diaper, may be treated with ammonia oxidizing bacteria. Because diapers are designed to hold and contain urine and feces produced by incontinent individuals, the urea in urine and feces can be hydrolyzed by skin and fecal bacteria to form free ammonia which is irritating and may cause diaper rash. Incorporation of bacteria that metabolize urea into nitrite or nitrate may avoid the release of free ammonia and may release nitrite and ultimately NO which may aid in the maintenance of healthy skin for both children and incontinent adults. The release of nitric oxide in diapers may also have anti-microbial effects on disease causing organisms present in human feces. This effect may continue even after disposable diapers are disposed of as waste and may reduce the incidence of transmission of disease through contact with soiled disposable diapers. The addition of the ammonia oxidizing bacteria to the diaper is beneficial when realizing that cleaning a soiled infant can remove ammonia oxidizing bacteria faster than they can proliferate, leaving only heterotrophic urea hydrolyzing bacteria on the skin. The epidemic of infant deaths due to Sudden Infant Death Syndrome, or SIDS, in the 1980's was approximately coincident with the widespread use of disposable diapers. The "back to sleep" program where infants are put to sleep on their backs has greatly reduced the incidence of SIDS. The mechanism of the causal relationship between back sleeping and low SIDS incidence remains elusive, however, it may be due to the increased contact of infant skin with urine during sleep occurring while the infant is lying on its back. Victims of SIDS are often found with sweat soaked bed clothes which may be due to due to the infant's vain attempt to increase nitric oxide formation during asphyxiation by sweating, rather than due to overheating as is conventionally thought.

Another article of clothing that can be so treated is the tampon. During a woman's menstrual period, secretions are generated which under certain circumstances can support the growth of heterotrophic disease causing bacteria such as those that cause toxic shock. Just as topically applied acidified nitrite has been shown to be curative for yeast infections of the skin, it is expected that vaginal application of these bacteria should be curative and preventative of vaginal yeast infections. By rendering the vagina less hospitable to disease causing organisms, the incidence of transmission of sexually transmitted diseases can be reduced.

Vaginal use of these bacteria by a woman may also enhance the sexual performance of a male partner by providing additional nitric oxide to her partner's sexual organ during sexual intercourse. Just as the nitrite in saliva provides the basis for the folk remedy for impotence, that of applying saliva to the male sexual organ, the stimulatory effect of the application of saliva to the female genitalia may also have its basis in the nitrite content of saliva. The present invention by enhancing the production of nitric oxide may provide a similar benefit in enhancing the sexual function of both men and women.

Other articles of clothing such as, for example, shoes, shoe inserts, pajamas, sneakers, belts, hats, shirts, underwear, athletic garments, helmets, towels, gloves, socks, bandages, and the like, may also be treated with ammonia oxidizing bacteria. Bedding, including sheets, pillows, pillow cases, and blankets may also be treated with the bacteria. In one embodiment of the invention, areas of skin that cannot be washed for a period of time may also be contacted with ammonia oxidizing bacteria. Specifically, skin enclosed in orthopedic casts which immobilize injured limbs during the healing process, and areas in proximity to injuries that must be kept dry for proper healing such as stitched wounds may benefit from contact with the ammonia oxidizing bacteria.

It is contemplated that articles worn about the head and scalp may be treated with ammonia oxidizing bacteria. Nitric oxide formed on the hair, away from the skin surface, may be captured in a hat, scarf or face mask and directed into inhaled air.

Individuals having a reduced bathing frequency, such as astronauts, submarine crew members, military personnel during a campaign, civilian workers in remote locations, refugees, bedridden individuals and many others may maintain healthier skin by maintaining skin bacteria according to the present invention. Bed sores are a common factor deriving from disturbances to blood flow. It is expected that the present invention may augment and normalize inadequate circulation problems.

Another aspect of the invention includes the use of the bacteria to inhibit the growth of heterotrophic bacteria. Body odor derives, in part, from bacterial metabolites on the skin. The development of skin odor in a day or so indicates that fast growing heterotrophic bacteria generate the odoriferous compounds. Ammonia oxidizing bacteria, by inhibiting the growth of the heterotrophic bacteria, may decrease the odor produced. Thus the present invention may also be used to reduce body odor, and may be used alone or in conjunction with other deodorant type cosmetic preparations.

In another embodiment, garments such as, for example, condoms, and codpieces may be treated with the proper bacteria. It is known that the male sexual organ requires nitric oxide for proper function during sexual intercourse. The stimulation from nitric oxide generation through wearing the articles may be beneficial for male subjects contemplating sexual acts. Similarly, the treatment of fabric coverings of furniture used for sexual activities would also be advantageous, such as, for example, sheets, blankets, slip covers, pillow cases.

Ammonia oxidizing bacteria may be located on a surface of the article directly contacting the surface of the subject. Alternatively, the bacteria may be exposed to bodily fluids but not directly in contact the surface of the subject. In particular, a diaper, tampon, or bandage may have an inner layer treated with the ammonia oxidizing bacteria, and at least one layer that is permeable to bodily fluids, nitric oxide, and or nitric oxide precursors. These layers need not be permeable to bacteria. Because the ammonia oxidizing bacteria cannot utilize compounds other than ammonia for energy, they cannot infect a wound. Although they may be allergenic, the inhibition of growth of heterotrophic bacteria may outweigh the potential for allergy.

It is contemplated that different bacteria will be most suitable for different applications. Thus bacteria adapted for very high levels of nitrite production may be ideal for use in diapers, animal bedding, and other non-contact applications. High nitrite levels would also be useful for protecting skin from infections during extended safaris in tropical environments, for military type applications, or for the enhancement of performance of elite athletes, human and non-human vertebrate.

While it is expected that the autotrophic ammonia oxidizing bacteria will be the most active at producing nitric oxide and nitric oxide precursors, other bacteria producing lessor amounts may be used as well. These may be desired in some circumstances when, for example, better control of the nitric oxide production is needed. Other bacteria can be included for other purposes, such as, for example, to control the pH through production of acid.

Further modification and equivalents herein disclose will occur to persons skilled in the art using no more than routine experimentation, and all such modifications and equivalents are believed to be within the spirit and scope of the invention as defined by the following claims.

What is claimed is:

1. A method of supplying nitric oxide to a subject comprising: applying ammonia oxidizing bacteria to a surface of the subject in an effective amount to cause the bacteria to metabolize a component selected from the group consisting of ammonia, ammonium salts and urea on the surface into any of the nitric oxide, a nitric oxide precursor, or combinations thereof.

2. The method of claim 1, wherein the act of applying the bacteria comprises applying the bacteria in a carrier.

3. The method of claim 1, wherein the act of applying the bacteria comprises applying a bacteria selected from the group consisting of any of *Nitrosomonas, Nitrosococcus, Nitrosospira, Nitrosocystis, Nitrosolobus, Nitrosovibrio*, and combinations thereof.

4. The method of claim 1, wherein the act of applying the bacteria to a surface comprises applying the bacteria to skin, hair, or a combination thereof.

5. The method of claim 1, wherein the act of applying the bacteria comprises applying a substantially homogeneous autotrophic culture of bacteria.

6. The method of claim 1, wherein the act of applying the bacteria comprises:
   applying the bacteria to an article;
   contacting the article with the surface of the subject; and
      transferring at least a portion of the bacteria from the article to the surface of the subject.

7. The method of claim 1, wherein the act of applying the bacteria comprises applying the bacteria mixed with an acid.

8. The method of claim 1, wherein the act of applying further comprises metabolizing any of urine, feces, blood, wound secretions, menstrual secretions, vaginal secretions, topically applied mixtures, and combinations thereof.

9. The method of claim 1, further comprising the act of applying a compound selected from the group consisting of perspiration, urea, nitrite, lactic acid, nitrate, salt, iron salts, ammonium salts, and combinations thereof, to the surface of the subject.

10. The method of claim 1, wherein the act of applying the bacteria comprises applying the bacteria to a subject that is a non-human vertebrate.

11. The method of claim 1, further comprising:
   applying at least one of urea or mineral salts to the surface of the subject in an effective amount to stimulate growth of the bacteria.

12. The method of claim 4, wherein the act of applying the bacteria to a surface of a subject includes applying the bacteria to the skin, hair, or a combination thereof, of a human.

13. The method of claim 4, wherein the act of applying the bacteria to the surface of the subject comprises applying the bacteria to the surface of the subject having a disorder selected from any of a vascular disease, impotence, infertility, or combinations thereof.

14. The method of claim 6, wherein the act of contacting the article with the surface of the subject further comprises contacting a fluid excretion from the surface of the subject with the bacteria.

15. The method of claim 6, wherein the act of applying the bacteria to an article comprises applying the bacteria to an article of clothing.

16. The method of claim 6, wherein the act of applying the bacteria mixed with an acid comprises applying the bacteria mixed with lactic acid.

17. The method of claim 9, wherein the acts of applying the compound and the bacteria include applying compound and the bacteria in a mixture.

18. The method of claim 10, wherein the act of applying the bacteria to the surface of the non-human vertebrate comprises:
applying the bacteria to any of skin, feather, hair, fur, scale or combinations thereof.

19. The method of claim 12, wherein the act of applying the bacteria comprises applying the bacteria to an underarm surface.

20. The method of claim 15, wherein the act of applying the bacteria to the article of clothing comprises the acts of:
wearing the article and impregnating the article with the bacteria.

21. The method of claim 15, wherein the act of applying the bacteria to the article of clothing comprises the acts of: wearing the article and coating the article with the bacteria.

22. The method of claim 15, wherein act of applying the bacteria comprises applying the bacteria to a diaper.

23. The method of claim 15, wherein the act of applying the bacteria comprises applying the bacteria to an article of clothing selected from the group consisting of shoe, sneaker, belt, hat, undergarment, pajama, athletic garment, sock, shoe insert, bandage, face mask, scarf, tampon, and condom.

24. The method of claim 18, wherein the act of applying the bacteria comprises applying the bacteria to any of bedding, litter, an article of clothing, or a habitat.

25. The method of claim 20, wherein the act of impregnating the article includes contacting the article with a culture medium containing the bacteria.

26. The method of claim 25, wherein the act of contacting the article with a culture medium containing the bacteria comprises applying an animal manure.

27. The method of claim 25, wherein the act of contacting the article with a culture medium containing the bacteria comprises contacting the article with a substantially pure culture of bacteria.

28. The method of claim 1, wherein the act of applying the bacteria comprises:
applying the ammonia oxidizing bacteria to the surface of the subject in an amount effective to metabolize a normal bodily secretion on the surface into any of nitric oxide, nitric oxide precursors, or combinations thereof.

29. The method of claim 28, wherein the act of applying bacteria comprises applying the bacteria to the skin between intervals of bathing.

30. The method of claim 28, wherein the act of metabolizing a normal constituent of skin secretion comprises metabolizing a component of perspiration.

31. The method of claim 29, wherein the act of applying the bacteria between intervals of bathing includes applying the bacteria at an interval of at least about one day.

32. The method of claim 30, wherein the act of metabolizing comprises metabolizing a component of perspiration selected from the group consisting of urea, nitrite, lactic acid, nitrate, salt, iron salts, ammonium salts, and combinations thereof.

33. The method of claim 29, wherein the act of applying the bacteria between intervals of bathing comprises applying the bacteria at an interval that is greater than or equal to about one week.

34. The method of claim 29, wherein the act of applying the bacteria is applied to a subject who lacks bathing facilities, is immobile, or has a bandage.

35. The method of claim 28, wherein the act of applying the bacteria comprises locally applying the bacteria to genitalia.

36. The method of claim 35, wherein the act of applying the bacteria includes locally applying the bacteria to a penis.

37. The method of claim 35, where in the act of applying the bacteria comprises locally applying the bacteria to a vagina.

38. The method of claim 1, further comprising applying a component selected from the group consisting of urea, ammonium salts, sodium, potassium, magnesium, calcium, phosphate, chloride, sulfate, trace mineral salts, iron, copper, zinc, cobalt, manganese, molybdenum, buffers, and combinations thereof to the surface of the subject in an effective amount to stimulate growth of the bacteria.

39. A topical preparation for application to a surface of a subject comprising ammonia oxidizing bacteria that metabolizes perspiration when present, into any of nitric oxide, nitric oxide precursors, or combinations thereof.

40. The preparation of claim 39, wherein the preparation is any of a cosmetic composition, a body deodorant, or an athletic preparation.

41. The preparation of claim 39, wherein the bacteria is selected from the group consisting of *Nitrosomonas, Nitrosococcus, Nitrosospira, Nitrosocystis, Nitrosolobus, Nitrosovibrio*, and combinations thereof.

42. The preparation of claim 39, wherein the component of perspiration is selected from the group consisting of urea, nitrite, lactic acid, nitrate, salt, iron salts, ammonium salts, and combinations thereof.

43. The preparation of claim 40, further comprising at least one component selected from the group consisting of water, mineral oil, coloring agent, perfume, aloe, glycerin, sodium chloride, pH buffers, UV absorbing agents, silicone oil, natural oil, vitamin E, herbal concentrates, Lactic acid, citric acid, talc, clay, calcium carbonate, magnesium carbonate, zinc oxide, starch, urea, nitrite, nitrate, iron salts, ammonium salts, and combinations thereof.

44. The preparation of claim 40, wherein the preparation is any of powder, cream, stick, aerosol, or salve.

45. The preparation of claim 39, wherein the surface of the subject is of a human being.

46. The preparation of claim 39, further comprising a component selected from the group consisting of water, mineral oil, coloring agent, perfume, aloe, glycerin, sodium chloride, pH buffers, UV absorbing agents, silicone oil, natural oils, vitamin E, herbal concentrates, lactic acid, citric acid, talc, clay, calcium carbonate, magnesium carbonate, zinc oxide, starch, urea, nitrite, lactic acid, nitrate, iron salts, ammonium salts, and combinations thereof.

47. The preparation of claim 39, further comprising:
at least one compound selected from the group consisting of urea, ammonium salts, sodium, potassium, magnesium, calcium, phosphate, chloride, sulfate, trace mineral salts, iron, copper, zinc, cobalt, manganese, molybdenum, buffers, and combinations thereof.

* * * * *